US00PP14232P39

(12) United States Plant Patent
Crowder

(10) Patent No.: US PP14,232 P3
(45) Date of Patent: Oct. 14, 2003

(54) HOSTA PLANT NAMED 'THUNDERBOLT'

(50) Latin Name: *Hosta*
Varietal Denomination: Thunderbolt

(75) Inventor: Allen Rick Crowder, Hickory, NC (US)

(73) Assignee: Hawksridge Farms Inc., Hickory, NC (US)

( * ) Notice: Subject to any disclaimer, the term of this patent is extended or adjusted under 35 U.S.C. 154(b) by 43 days.

(21) Appl. No.: 10/055,217

(22) Filed: Oct. 29, 2001

(65) Prior Publication Data

US 2003/0084494 P1 May 1, 2003

(51) Int. Cl.[7] ..... A01H 5/00

(52) U.S. Cl. ..... Plt./353
(58) Field of Search ..... Plt./353

(56) References Cited

U.S. PATENT DOCUMENTS

PP13,080 P2 * 10/2002 Hansen ..... Plt./353

* cited by examiner

*Primary Examiner*—Bruce R. Campell
*Assistant Examiner*—Susan B. McCormick
(74) *Attorney, Agent, or Firm*—Mark P. Bourgeois

(57) ABSTRACT

A new cultivar of Hosta plant named 'Thunderbolt' that is characterized by vigor, white flowers in late spring and large variegated blue-green leaves with centers that change in color from golden to cream-white as the plant matures. In combination these traits set 'Thunderbolt' apart from all other existing varieties of Hosta known to the inventor.

3 Drawing Sheets

Botanical classification: Hosta.
Variety denomination: 'Thunderbolt'.

BACKGROUND OF THE INVENTION

The present invention relates to a new and distinct cultivar of plaintain lily that is grown for its vigorous growth, white flowers and thick, furrowed, variegated leaves. The new cultivar is known botanically as Hosta and will be referred to hereinafter by the cultivar name 'Thunderbolt'.

'Thunderbolt' was discovered by the inventor in a cultivated area of Hickory, N.C. in 1998 as a sport of the parent plant *Hosta sieboldiana* 'Elegans'. 'Thunderbolt' was selected, by the inventor, for its unique variegated leaves with wide blue-green margins and narrow cream-white centers. As a young plant the leaves are blue-green with golden centers and as the plant matures the leaf centers become cream-white and the margins darken. The plant most similar to 'Thunderbolt' are the parent plant *Hosta sieboldiana* 'Elegans' (unpatented) and Hosta 'Dream Weaver' (unpatented). 'Thunderbolt' differs from 'Elegans' in its bluer, thicker leaves and its variegation that exhibits a wider green margin and narrow cream-white center. 'Thunderbolt' also grows more vigorously than the parent plant 'Elegans', which is slow-growing. 'Thunderbolt' is suitable for planting in full shade or partial shade. 'Thunderbolt' differs from 'Dream weaver' in that it has leaves with a wider margin and narrower cream-white center. The leaves of 'Thunderbolt' are more deeply furrowed than those of 'Dream Weaver'.

Asexual reproduction of the new cultivar was first accomplished by the inventor in a cultivated area of Hickory, N.C. in 1998 using tip cuttings. The characteristics of the new cultivar have been determined stable and are reproduced true to type in successive generations.

SUMMARY OF THE INVENTION

The following traits have been repeatedly observed and represent the characteristics of the 'Thunderbolt'. These traits in combination distinguish the new cultivar from all other commercial varieties known to the inventor. 'Thunderbolt' has not been tested under all possible conditions and phenotypic differences may be observed with variations in environmental, climatic and cultural conditions.

1. Hosta 'Thunderbolt' exhibits large, furrowed leaves.
2. The leaves of Hosta 'Thunderbolt' are bluer and thicker than the parent plant.
3. Hosta 'Thunderbolt' exhibits leaves with blue-green margins and golden centers in spring that turn to cream-white centers as the plant matures.
4. Hosta 'Thunderbolt' exhibits white flowers in late spring.
5. Hosta 'Thunderbolt' is a vigorous grower.
6. Hosta 'Thunderbolt' is hardy in USDA Zones 3–8.

BRIEF DESCRIPTION OF THE DRAWINGS

The accompanying color laser prints are copies of original photographs illustrating the distinguishing traits of 'Thunderbolt'.

Sheet 1 illustrates the golden centers on the young foliage.

Sheet 2 illustrates the cream-white centers and dark blue-green margins of mature foliage.

Sheet 3 shows 'Thunderbolt' in flower. All photographs were taken in Hickory, N.C. of plants grown in one-gallon containers out-of-doors. All photographs and laser copies have been made using conventional techniques and although colors may appear different from actual colors due to light reflectance they are as accurate as possible by conventional photography and laser copying.

BOTANICAL DESCRIPTION OF THE PLANT

The following is a detailed description of the new cultivar at two years and grown in one-gallon containers out-of-doors. Data was recorded in Arroyo Grande, Calif. The color determinations are in accordance with The R.H.S. Colour Chart of The Royal Horticultural Society, London, England, except where general color terms of ordinary dictionary significance are used. 'Thunderbolt' is no more susceptible to pest and disease problems than other Hosta varieties. Growing conditions are similar to other Hosta varieties.

Botanical classification: *Hosta sieboldiana* 'Thunderbolt'.
Commercial classification: Herbaceous perennial.
Common name: Plaintain lily.
Use: Container or landscape plant.
Cultural requirements: Plant in full shade or part shade, and plant in organically enriched soil.
Parentage: Hosta 'Thunderbolt' is a branch sport. The parent plant is *Hosta sieboldiana* variety 'Elegans'.
Plant description:
*Flowering season.*—Late spring and into summer.
*Plant habit.*—Upright.
*Vigor.*—Vigorous.
*Growth rate.*—Flowering stems grow at a rate of 20 cm. per month.
*Plant shape.*—Broad inverted triangle.
*Height.*—75 cm. in height.
*Width.*—70 cm. in width.
*Hardiness.*—USDA Zones 3–8.
*Propagation.*—Propagation is accomplished by tip cuttings and/or division.
*Time to initiate roots.*—3 weeks.
*Range of average nighttime temperatures.*—7–14° Centigrade.
*Range of average daytime temperatures.*—14–27° Centigrade.
*Crop time.*—Approximately 20 weeks are required to produce a finished one-gallon from a rooted cutting.
Stem:
*Shape.*—Cylindrical.
*Lateral stem dimensions.*—75 cm. in length and 5 mm. in diameter.
*Stem strength.*—Strong.
*Stipules, tendrils or thorns.*—Absent.
*Stem surface.*—Glabrous and dull.
*Pubescence.*—Absent.
*Stem color.*—Striped yellow-green 158C and 144A.
*Branching habit.*—Basal rosette.
*Internode length.*—No internodes. Leaves are in a basal rosette with one reduced leaf on each flowering stem.
Foliage:
*Type.*—Evergreen.
*Compound or single.*—Single.
*Quantity.*—Approximately 13 per rosette.
*Durability of foliage to stress.*—Moderate.
*Shape.*—Broad cordate to broad ovate.
*Division.*—Simple.
*Apex.*—Apiculate.
*Base.*—Cordate to attenuate.
*Venation.*—Parallel.
*Vein color* (*adaxial and abaxial surfaces*).—In green areas the veins are 137B and in golden areas the veins are 160B.
*Margins.*—Entire.
*Surface.*—Dull and furrowed.
*Pubescence.*—Absent.
*Arrangement.*—Alternate in basal rosette.
*Attachment.*—Petiolate.
*Petiole dimensions.*—1.5 cm. in width and 7 mm. in length.
*Petiole shape.*—V-shaped in cross section.
*Petiole color.*—Yellow and green striped colors 150D and 143A.
*Leaf dimensions.*—19 cm. in length and 15 cm. in width.
*Leaf color on young plants* (*adaxial and abaxial surfaces*).—The center is closest to 160B and the margins are 133D.
*Leaf color of mature plants* (*adaxial and abaxial surfaces*).—The center is 158C and the margins are closest to 133B.
*Fragrance.*—Absent.
*Other foliage characteristics.*—Each flowering stem carries one reduced leaf halfway up the stem. This leaf is 11 cm. in width and 6.7 cm. in length.
Flowers:
*Shape.*—Campanulate.
*Type of inflorescence.*—Raceme.
*Inflorescence dimensions.*—25 cm. in height and 7.5 cm. in width.
*Quantity of flowers per inflorescence.*—Approximately 29 flowers per inflorescence.
*Quantity of flowers per lateral stem.*—Approximately 29 flowers per lateral stem.
*Quantity of flowers per plant.*—Approximately 87.
*Flower arrangement.*—Flowers alternately placed in raceme.
*Persistent or self-cleaning.*—Persistent.
*Aspect.*—Facing outward and slightly pendulous.
*Bloom period.*—Continuously blooming from late spring into July.
*Fragrance.*—Faint sweet scent.
*Bud dimensions.*—3.20 cm. in length and 1.10 cm. in diameter.
*Bud shape.*—Narrow obovate.
*Bud color.*—85D.
*Flower color.*—155A.
*Flower dimensions.*—2.6 cm. in diameter and 4.7 cm. in height.
*Rate of opening* (*per flowering stem*).—20% open all at once and within 4 weeks the remaining flowers have opened.
*Tepals.*—Six in number.
*Tepal shape.*—Oblanceolate.
*Tepal apex.*—Acute.
*Tepals fused or unfused.*—Base fused and upper 60% of tepals are free.
*Tepal margin.*—Entire.
*Tepal surface.*—Dull and glabrous.
*Tepal dimensions.*—4.6 cm. in length and 1.2 cm. in width.
*Petaloids.*—None.
*Calyx shape.*—Campanulate.
*Calyx dimensions.*—4.6 cm. in length and 2.6 cm. in diameter.
*Sepals.*—No separate sepals, only tepals.
*Peduncle dimensions.*—No peduncles, flowers appear directly at flowering stem.
*Pedicel.*—Present.
*Pedicel color.*—A combination of 138B and 155C.
*Pedicel strength.*—Strong.
*Pedicel dimensions.*—2 mm. in diameter and 1.7 cm. in length.
*Pedicel angle.*—40–65°.

*Bract.*—One at the base of each pedicel.
*Bract dimensions.*—2 cm. in length and 1 cm in width.
*Bract color.*—85D.
*Bract shape.*—Broad elliptic.
*Bract apex.*—Acute.
*Bract base.*—Cuneate.

Reproductive organs:
*Stamens.*—Six in number.
*Stamen color.*—155C.
*Stamen dimensions.*—3.50 cm. in length and 1 mm. in width.
*Anther color.*—21A.
*Amount of pollen.*—Low.
*Pollen color.*—21A.
*Anther shape.*—Oblong.
*Anther attachment.*—Dorsifixed.
*Anther dimensions.*—4 mm. in width and 5 mm. in length.
*Pistil.*—One in number.
*Pistil dimensions.*—4.8 cm. in length and 1 mm. in diameter.
*Pistil color.*—155C.
*Stigma shape.*—Crested.
*Stigma color.*—155C.
*Style color.*—155C.
*Style dimensions.*—4.7 cm. in length and 1 mm. in diameter.
*Ovary color.*—151C.
*Ovary dimensions.*—0.50 cm. in height and 4 mm. in diameter.
*Ovary shape.*—Oblong.

Seed production:
*Quantity of seed.*—Approximately 12 seeds per fruit.
*Seed color.*—202A.
*Seed dimensions.*—1 cm. in length and 3.5 mm. in diameter.
*Seed shape.*—Flattened oval.
*Texture.*—Dull and slightly ribbed.
*Quantity of fruit per lateral branch.*—Approximately 25.
*Quantity of fruit per plant.*—Approximately 75.
*Fruit dimensions.*—2.7 cm. in length and 7 mm. in diameter.

I claim:

1. A new and distinct cultivar of Hosta plant named 'Thunderbolt' as herein described and illustrated.

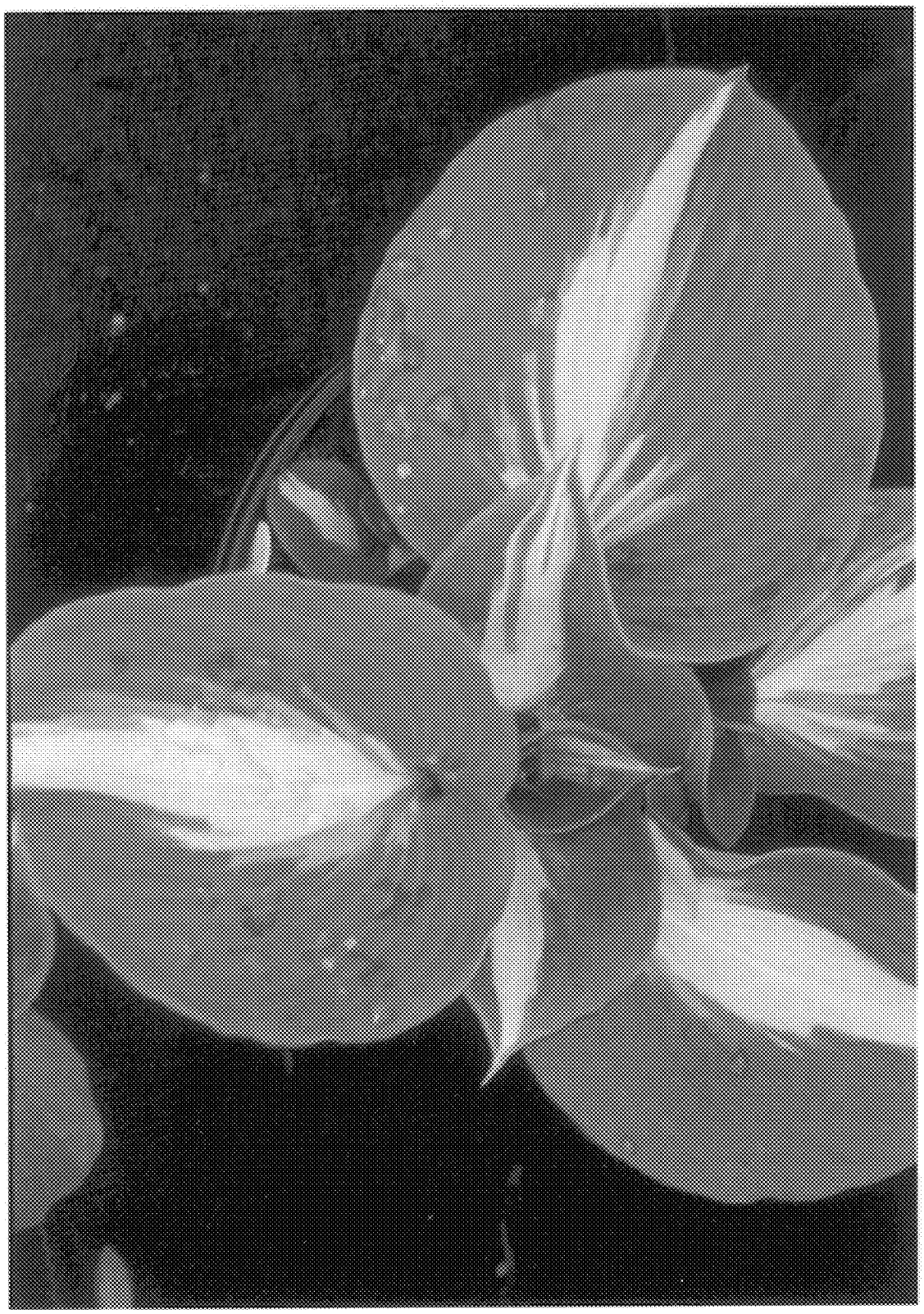

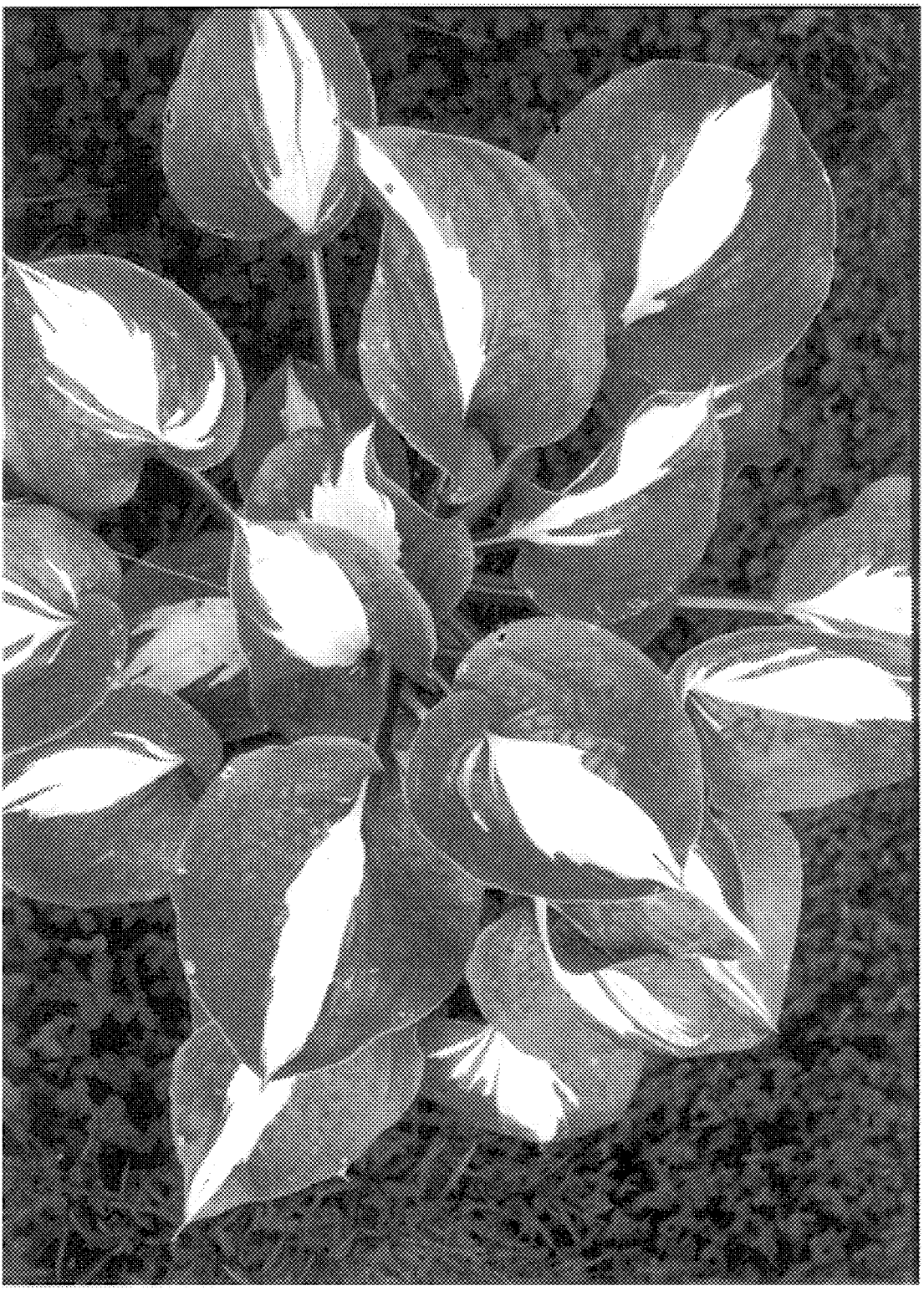

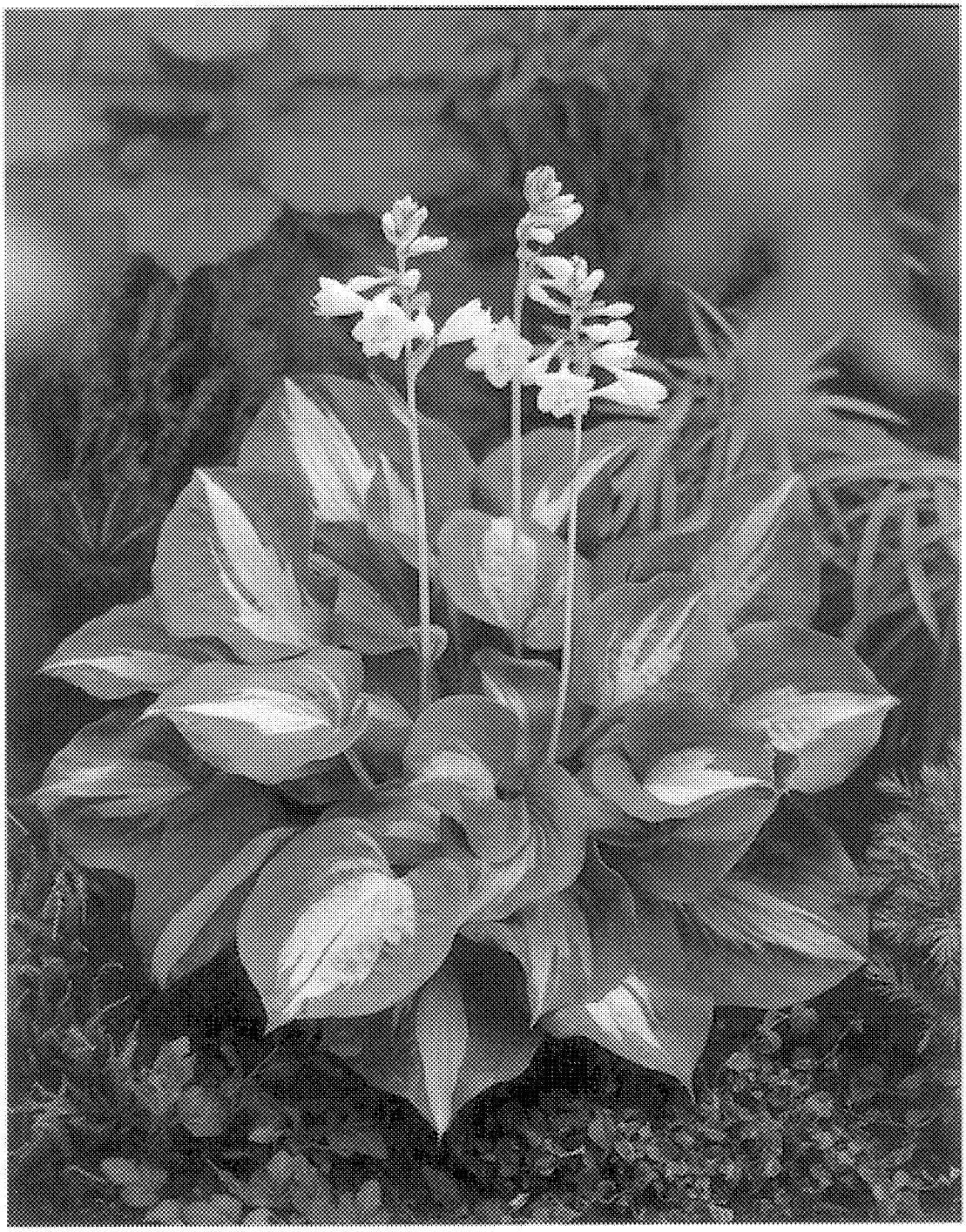

* * * * *